United States Patent [19]

Miner, II

[11] Patent Number: 5,578,069
[45] Date of Patent: Nov. 26, 1996

[54] ELECTRODE DEPLOYMENT MECHANISM AND METHOD USING ARTIFICIAL MUSCLE

[75] Inventor: William D. Miner, II, Santa Clara, Calif.

[73] Assignee: Vnetritex, Inc., Sunnyvale, Calif.

[21] Appl. No.: 568,046

[22] Filed: Dec. 6, 1995

[51] Int. Cl.$^6$ .................................................. A61N 1/39
[52] U.S. Cl. ........................ 607/126; 607/128; 607/122
[58] Field of Search .................................. 607/119, 122, 607/123, 126, 128

[56] References Cited

U.S. PATENT DOCUMENTS

| Re. 35,068 | 10/1995 | Tanaka et al. | 523/300 |
|---|---|---|---|
| 5,010,894 | 4/1991 | Edhag | 128/785 |
| 5,190,052 | 3/1993 | Schroeppel | 128/786 |
| 5,250,167 | 10/1993 | Adolf et al. | 204/299 |
| 5,358,516 | 10/1994 | Myers et al. | 607/116 |
| 5,411,546 | 5/1995 | Bowald et al. | 607/126 |
| 5,423,864 | 6/1995 | Ljungstroem | 607/5 |
| 5,449,381 | 9/1995 | Imran | 607/122 |

OTHER PUBLICATIONS

"Current Concepts for Selecting the Location, Size and Shape of Defibrillation Electrodes", Ideker, et al., *PACE*, vol. 14, Feb. 1991, Part I, pp. 227–240.

"Improved Internal Defibrillation Efficacy with a Biphasic Waveform", Fain, et al., *American Heart Journal*, vol. 117, No. 2, Feb. 1989, pp. 358–364.

"Finite Element Analysis of Cardiac Defibrillation Current Distributions", Sepulveda, et al., *IEEE Transactions on Biomedical Engineering*, vol. 37, No. 4, Apr. 1990, pp. 354–365.

"Electrochemical Muscles: Micromachining Fingers and Corkscrews" Smela, et al., *Adv. Materials*, vol. 5, No. 9, 1993, pp. 630–632.

"Electrostriction of Highly Swollen Polymer Gel: Possible Application for Gel Actuator", Hirai, et al., *Journal of Applied Polymer Science*, vol. 53, 1994, pp. 79–84.

"Implantable Cardioverter Defibrillator Lead Technology: Improved Performance and Lower Defibrillation Thresholds", *PACE*, vol. 18, Mar. 1995, Part II, pp. 548–559.

"Electro-Driven Chemomechanical Polymer Gel as an Intelligent Soft Material", Okuzaki, et al., *J. Biomaterial Science, Polymer Edition*, vol. 5, No. 5, 1994, pp. 485–495.

"Continuum Electromechanics of Ionic Polymeric gels as artificial Muscles for Robotic Applications" Shahinpoor, *Smart Material Struct.*, 3, 1994, pp. 367–372.

"Plastic Gels uses Extend to 'Muscles', Valves", *C&EN*, Jan. 8, 1990, pp. 30–31.

*Primary Examiner*—William E. Kamm
*Assistant Examiner*—Carl H. Layno
*Attorney, Agent, or Firm*—Steven M. Mitchell; Mark J. Meltzer; M. Elizabeth Bush

[57] ABSTRACT

A lead having a defibrillation electrode that is deployed for defibrillation using artificial muscle. In an undeployed position, the defibrillation electrode is small in diameter so as to be easily implanted pervenously and nonobstructive to cardiac contraction and blood flow. In a deployed position the defibrillation electrode is larger in diameter for defibrillation shock delivery. Thus, the electrode forces an increased amount of current to flow through the heart muscle during shock delivery to depolarize the majority of the cardiac tissue with a minimum of energy, while not obstructing blood flow at other times when not used for energy delivery.

26 Claims, 3 Drawing Sheets

ELECTRODE DEPLOYMENT MECHANISM AND METHOD USING ARTIFICIAL MUSCLE

FIELD OF THE INVENTION

The present invention relates generally to cardiac defibrillation devices, and more specifically to an implantable lead which provides a means for directing energy to the heart muscle during defibrillation.

BACKGROUND OF THE INVENTION

It is desirable to reduce the size of an implantable cardioverter/defibrillator (ICD) in order to improve patient comfort, reduce risk of erosion through the skin, and facilitate pectoral placement. Because the batteries and capacitors account for a large portion of the defibrillator, reducing the defibrillation threshold (DFT), or the amount of energy, voltage, or current required to defibrillate the heart, is key to allowing the device size to be reduced. Using less energy to defibrillate has the added benefit of improving patient comfort and reducing trauma to the patient's cardiac conduction system, as well as prolonging battery and device life.

Many techniques have been used in the past to reduce defibrillation thresholds. These include the use of modified electrodes, described by Ideker et al. in "Current Concepts for Selecting the Location, Size and Shape of Defibrillation Electrodes," *PACE* 1991, 14:227–240 and by Lang et al. in "Implantable Cardioverter Defibrillator Lead Technology: Improved Performance and Lower Defibrillation Thresholds," *PACE* 1995, 18:548–559, and the use of biphasic waveforms, described by Fain et al. in "Improved Internal Defibrillation Efficacy with a Biphasic Waveform," *American Heart Journal* 1989, 117:358–364.

Right ventricular (RV) and superior vena cava (SVC) transvenous electrodes are situated in blood, which has nearly three times the conductivity of cardiac muscle. In a discussion of current shunting by the blood during defibrillation between RV and SVC leads in "FEA of Cardiac Defibrillation Current Distribution," *I.E.E.E. Biomed. Trans.*, Vol. 37, No. 4, April 1990 by N. G. Sepulveda, the amount of current shunted is approximated from finite element analysis studies to be nearly 50 percent. By directing the current directly through the heart wall without having it first pass through the blood, current shunting through the blood would be reduced. Also, because most of the potential drop occurs in the "near field" of the electrode, the closer an electrode is to the endocardium and the more surface of the electrode in contact with the endocardium, the more likely that the heart will see a higher potential gradient. Therefore, it is desirable to create a large shadow area and to substantially limit energy shunting through the blood pool during defibrillation to lower the DFT, while maintaining normal blood flow and normal heart motion when no therapy is being delivered.

Deployable defibrillation electrodes that are low profile during introduction into the heart, but that expand to form a relatively high surface area, have been described, such as in U.S. Pat. No. 5,010,894 to Edhag. The electrode head of this defibrillation electrode is formed by a plurality of outwardly-projecting, precurved flexible conductors, which serve as defibrillation surfaces. The proximal ends of the conductors are anchored adjacently in a common connection device at the same time as their distal ends are adjacently anchored to a second common connection device. Before the lead is introduced into a heart via a vein, the electrode head is stretched using a stylet so that the conductors are brought close to each other, thereby giving the electrode head a diameter which is only slightly larger than the diameter of the lead body. After the electrode head has been advanced into the heart, the stylet can be withdrawn, thereby permitting the conductors to expand laterally so as to resiliently press against the surrounding wall along a substantial portion of their length. Current applied through this defibrillation electrode can be evenly distributed to these conductors, which jointly form a relatively large defibrillation area. This can prevent burn damage to the surrounding heart wall. Low defibrillation thresholds can be achieved because the conductors can be evenly distributed inside the heart. Such a relatively large electrode head, however, can impede the flow of blood in the heart.

In U.S. Pat. No. 5,411,546 to Bowald et al., which is incorporated herein by reference in its entirety, a defibrillation electrode is in a nonexpanded state during implantation, and is radially expanded once in its desired permanent vascular location to conform to the walls of the blood vessel. Means for providing expandability are disclosed, including forming the electrode from a shape-memory metal which can be given a shape at a first temperature suitable for implantation, and assume a cylindrical shape at a second temperature, preferably at body temperature.

In U.S. Pat. No. 5,423,864 to Ljungstroem, which is incorporated herein by reference in its entirety, a defibrillation system includes a defibrillation electrode for intracardiac placement, which contains a flexible electrode cable with at least one elongate, electrically insulated conductor and at least one defibrillation surface disposed at the distal end of the electrode cable for delivering defibrillation pulses to the heart. The system further includes control components and circuitry for determining when defibrillation therapy is to be administered. By providing a large surface area intracardiac defibrillation electrode, current can be distributed so as to prevent damage to the heart. To provide such an electrode without impeding the blood flow during periods when it is not used to emit pulses, the electrode head is constructed so as to be expandable, and the defibrillator housing includes control elements and circuitry operable on the electrode head via the electrode cable to cause the electrode head to expand as needed, and to subsequently return to a non-expanded state. The two means disclosed for expanding the electrode head include a pump which pumps fluid through a channel in the electrode cable to and from a balloon, and a motorized spool from which a line or thread can be wound and unwound to collapse and expand leg components of an electrode. Presumably due to the large amount of energy expended in pumping the fluid through the channel, the electrode is left deployed until sinus rhythm is redetected. This may not be desirable in some cases, such as during the administration of CPR, since the expanded device would impede blood flow. Another drawback to this system is that a shock is delivered only after the expansion logic determines that the electrode head has been expanded; in the event that the expansion mechanism fails, no shock would be delivered. Another drawback to this system is that were the device to fail in the deployed position, blood flow would be seriously impeded. Still another drawback to the system in which a balloon is pumped with fluid is the possibility of hydrodynamic shock, due to the fast change of volume within the heart.

SUMMARY OF THE INVENTION

The present invention comprises an endocardial defibrillation lead having an "umbrella wire" or basketlike defibrillation electrode that expands inside of the ventricle or other chamber of the heart to direct energy to the heart muscle while minimizing shunting of energy through the blood within the heart chambers. Preferably, the electrode is deployed just before the defibrillation shock and returns to its original position afterwards.

The terms "artificial muscle" (AM) and "smart material", as used herein, refer to materials that have electrostrictive, electrokinetic, or chemomechanical properties. These materials include, but are not restricted to, poly(2-acrylamido-2-methylpropanesulfonic acid) (PAMPS) gel, polyacrylic acid plus sodium acrylate cross-linked with bisacrylamide (PAAM), and other polyelectrolyte gels.

In this invention, an electric field directly controls the local concentration of ions, changing the pH, and "stimulating" the AM to contract or expand. This process can be used on demand to deploy the electrode only as needed. It is a very controllable and repeatable system that uses little battery current. In contrast, to heat a temperature-controlled shape memory metal such as nickel titanium to deploy only when desired would require a substantial current. The applied voltage in the AM system pulls the ions to their respective poles to contract the AM, requiring very little current.

The electrode may be returned to its initial collapsed condition by simply removing the applied voltage, by reversing polarity of the applied voltage, or by using a spring.

It is therefore an object of this invention to provide an electrode deployment mechanism comprising artificial muscle and means for applying a voltage across it, causing the muscle to contract and the electrode to deploy.

It is another object to provide means for returning the deployable electrode to its initial collapsed condition.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
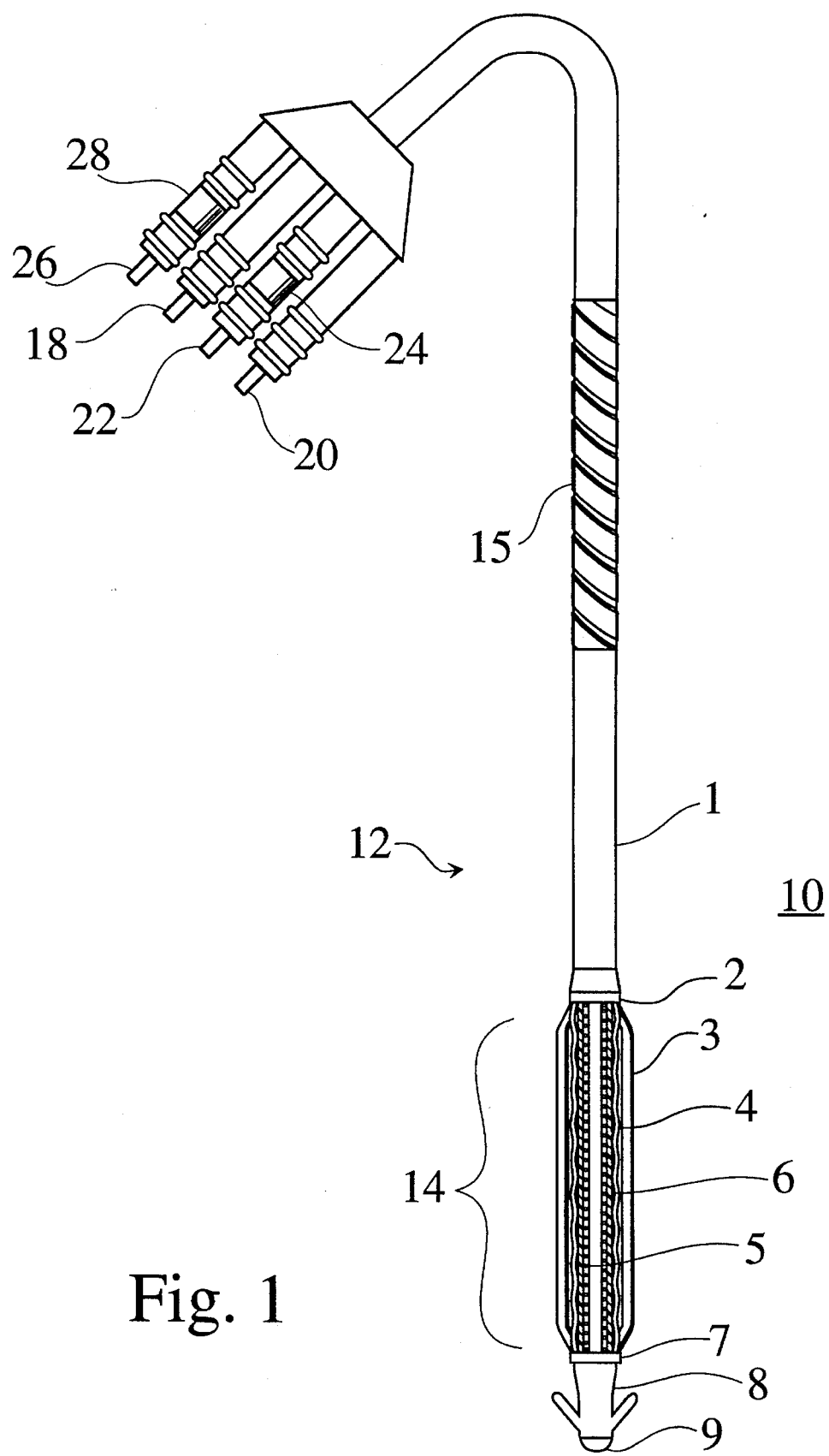
FIG. 1 is a perspective view of a lead of the present invention.

FIG. 1 shows a cylindrical transvenous defibrillation lead 10 having a lead body 1, a proximal defibrillation electrode 15, a sliding proximal ring 2 that forms a mechanical connection for the proximal end of an artificial muscle element 6, a plurality of deployable lead segments 3 forming an RV electrode 14, and a flexible protective sheath 4. Preferably three or more deployable lead segments 3 are used.

The deployment mechanism uses artificial muscle technology, such as that described in U.S. Pat. No. 5,250,167 to Adolf et al., which is incorporated herein by reference in its entirety. Other references describing artificial muscle technology include the following: Hirai et al., "Electrostriction of Highly Swollen Polymer Gel: Possible Application for Gel Actuator," *Journal of Applied Polymer Science*, Vol. 53, 79–84 (1994); Okuzaki et al., "Electro-driven Chemomechanical Polymer Gel as an Intelligent Soft Material," *J. Biomater. Sci. Polymer Edn*, Vol. 5, No. 5, pp. 485–495 (1994); Shahinpoor, "Continuum Electromechanics of Ionic Polymeric Gels as Artificial Muscles for Robotic Applications," *Smart Mater. Struct.* 3,(1994) 367–372; and Stinson et al., "Plastic Gels Uses Extend to 'Muscles,' valves," Jan. 8, 1990 *C &EN*, which are incorporated herein by reference in their entireties. This lead may be used with various combinations of transvenous, epicardial, and subcutaneous electrodes. According to recent literature, polyelectrolyte gels have been developed that have a reaction time of less than one second with an applied voltage of 10 V. This is well within the range to be practical for use in a defibrillation system using artificial muscle to deploy the electrode upon detection of fibrillation. Despite the fast deployment rate, a design using artificial muscle can result in little, if any, hydrodynamic shock within the heart. As used herein, artificial muscle "strands", "elements", and "fibers" are all synonymous with artificial muscle (AM).

Defibrillation electrode 14 formed by the deployable lead segments 3 is electrically isolated from proximal ring 2, and electrically coupled to defibrillation connector pin 18 and to sensing connector ring 24. An insulated or nonconductive return spring 5 works against proximal ring 2 to provide the force required to speed the return of electrode 14 to its resting or relaxed position when artificial muscle 6 is relaxed. Artificial muscle 6 is electrically isolated from the defibrillation electrode 14 and from the return spring 5. Return spring 5 may be provided with a coating such as parylene, a fluoropolymer, or ceramic for electrical isolation. The deployable lead segments 3 may be flexible or may provide some spring return force. The flexible protective sheath 4 protects the artificial muscle 6 and return spring 5 from being impeded by tissue growth. The artificial muscle strands 6 are strands of a "smart" polymer material that shorten (contract) or lengthen (expand) along the length of the strand when an appropriate potential is applied. A fixed distal ring 7 forms the mechanical connection and anchor for the distal end of the artificial muscle 6, the deployable lead segments 3, and the flexible protective sheath 4. The artificial muscle 6 is electrically connected to ring 2 at its proximal end and to ring 7 at its distal end. Rings 7 and 2 are electrically connected to a pin 26 and a ring 28 at the proximal end of lead 10. Lead 10 has typical tines 8 for passive fixation of the distal end of the lead and a pacing/sensing electrode 9 which is electrically coupled to connector pin 22 at the proximal end of the lead. Proximal defibrillation electrode 15 is electrically connected to pin 20.

As shown in FIG. 1, artificial muscle elements 6 are in their relaxed, noncontracted form, and segments 3 are in their normal state lying substantially parallel to lead body 1. A stylet is used to stiffen the lead for implant. Once the lead is in place in the right ventricle, it maintains this collapsed shape until it is needed for high voltage shock delivery.

Several variations are possible within the scope of the invention. For example, the proximal ring 2 may be fixed to the lead body 1, and the distal ring 7 may be sliding. In that case, the electrode would be deployed away from the distal end of the lead instead of toward it. As another alternative, deployable lead segments 3 may be provided with enough spring force with a bias to return to the undeployed condition so that return spring 5 is not necessary.

Highly motile smart materials, such as PAMPS, expand and contract differentially. When the polarity of the voltage applied is reversed, expanded material contracts and contracted material expands. Therefore, as yet another alternative, the electrode may be returned to its resting position (collapsed) quickly by reversing the polarity of the voltage across the artificial muscle, thereby obviating the need for the return spring.

Since many AM materials must be surrounded by an electrolyte in order to expand and contract with applied voltage, the artificial muscle may be isolated by flexible protective sheath 4 so as to form a tube containing an appropriate electrolyte around the AM. The insulation would be made of flexible, nonabrasive, biocompatible material of sufficient thickness and dielectric strength to provide adequate electrical insulation from the local potential gradient. During a defibrillation shock the electric field present between the SVC and RV electrodes would be much higher than the field presented for AM activation. However, the duration of the defibrillation pulse, typically less than 20 ms, does not give the AM enough time to react. Also, the AM is protected from any current shunting by the protective sheath 4. The insulation may be in the form of bellows which can contract and expand with the underlying artificial muscle. A composite material such as silicone rubber laminated with expanded polytetrafluoroethylene (ePTFE) which may be impregnated with a hydrogel or with a drug such as the steroid dexamethasone sodium phosphate to reduce tissue response to the material, may be used. The silicone layer provides an electrically insulating barrier, while the ePTFE minimizes fibrotic growth. Other examples of drugs which may elute from the insulation into the bloodstream and to adjacent tissues such as the endocardium include any suitable drug or combination of drugs intended to counter thrombus formation, fibrosis, inflammation, poor myocardial perfusion, ischemia, arrhythmias, or any combination of these.

Alternatively, the AM may not be insulated, and may use blood as the electrolyte. Optionally, the AM may be protected by flexible protective sheath 4 in the form of an open cell polymer, such as ePTFE, that would allow electrolytes through but would minimize fibrotic growth. Without an electrically insulative barrier surrounding the AM, the defibrillation electrode preferably would be designed to minimize the potential gradient seen by the AM, thereby having no effect on it. Alternatively, the defibrillation electrode may be designed to either extend the duration of the contraction of the AM or speed its recovery.

In a preferred embodiment, the defibrillation lead electrode of FIG. 1 is deployed only for the delivery of a defibrillation shock. In that case, the electrode may be larger to cover much of the cross section of the right ventricle, since it will not obstruct blood flow in its collapsed state when not being used to deliver defibrillation energy. However, the electrode is preferably short enough that the proximal end does not extend through the tricuspid valve when in its collapsed state. When the pulse generator is charging its capacitor(s) to deliver a high voltage defibrillation shock, it applies a voltage across pin 26 and ring 28, activating the artificial muscle to form an electrode having a large "shadow area" very close to the myocardium to direct current flow to the heart during the shock. Upon completion of the shock delivery, the electrode is collapsed to allow for normal function of the heart and normal blood flow.

It should be noted that even if the electrode should fail to completely deploy, the electrode is still functional, and a shock could be delivered in its collapsed state. In this configuration, the safety margin would be less and the likelihood of the shock effectively defibrillating the heart would be less for the same energy. Therefore, the defibrillator may be supplied with a detection means to detect whether the electrode is successfully deployed. It may then adjust the output to deliver a higher energy shock in the event that the electrode does not deploy or deploys only partially.

The electrode may be deployed manually during implantation for defibrillation threshold (DFT) testing. Typically, during DFT testing, an external defibrillator is used which may not have the capability of deploying the electrode. Therefore, the ability to manually deploy the electrode is useful. Alternatively, a voltage source may be supplied specifically to deploy the electrode during implant to test for defibrillation thresholds and to test the positioning and deployability of the electrode.

In order to keep the artificial muscle in good working order and break up any adhesions that may begin to form, the muscle may be exercised periodically, such as biweekly or monthly, without delivering a high voltage shock to the heart. The muscle may be made to contract fully or only partially, and may be timed to occur with certain events in the cardiac cycle, such as during filling of the ventricles.

Figure 2:
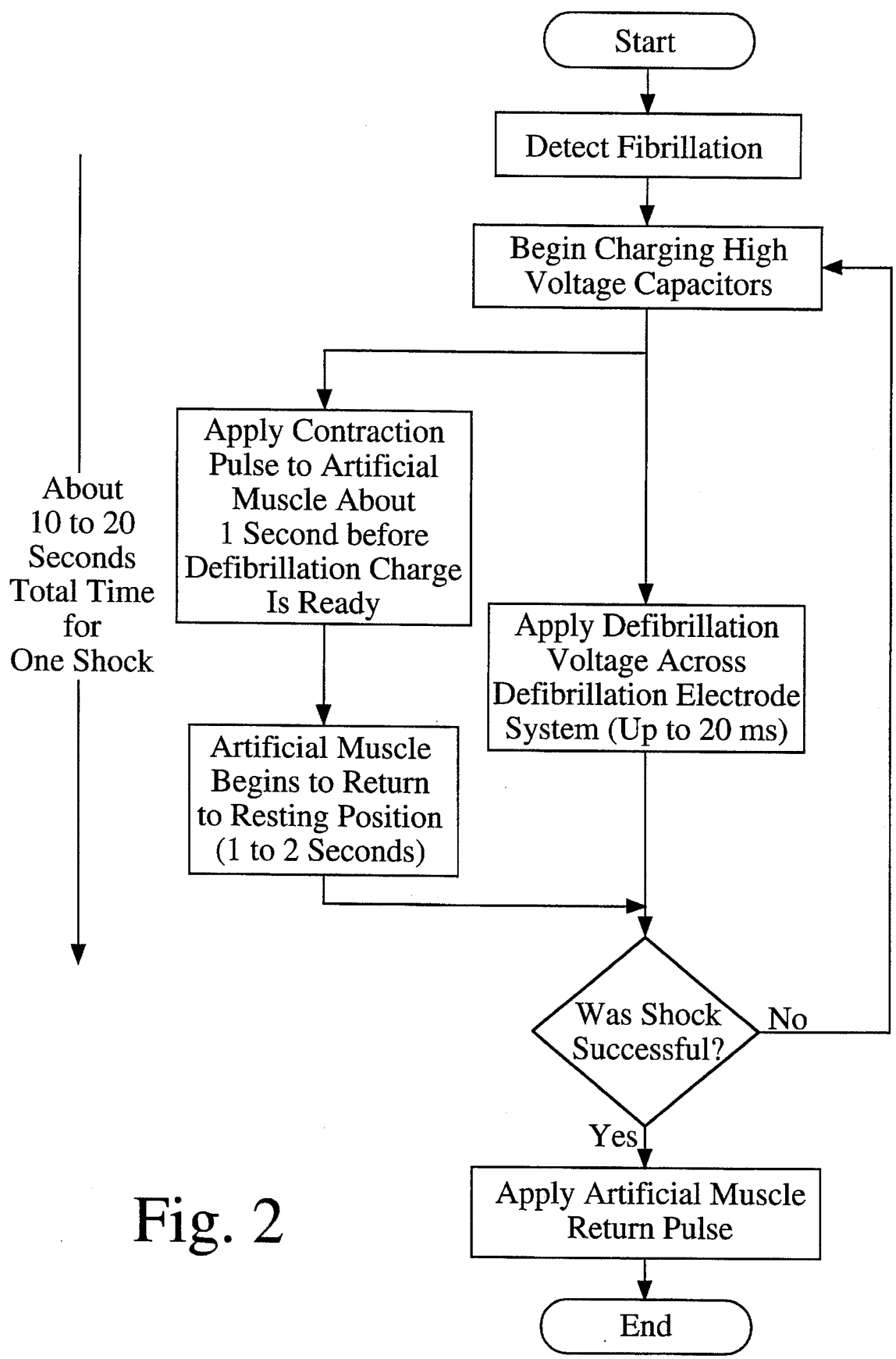
FIG. 2 is a flow chart illustrating the sequence of events followed in practicing the method of the present invention.

FIG. 2 provides a flow chart illustrating the sequence of events followed in practicing the method of the present invention. When fibrillation is detected, the high voltage defibrillation capacitors begin charging, which typically takes about 10 to 15 seconds. While the capacitors are charging, and to cause the artificial muscle to contract, a "contraction pulse", typically 10 volts or less, is supplied to the artificial muscle strands. The voltage used depends on the requirements of the particular material used for the artificial muscle, but preferably, the material chosen requires 10 volts or less to contract. The contraction pulse may be timed to cause the electrode to deploy near the end of the capacitor charge time. Once the artificial muscle has contracted sufficiently to deploy the defibrillation electrode (about one second), and optionally, after reconfirming fibrillation, the defibrillation pulse, typically 500 volts, is delivered. The electrode is then returned to its "rest" position within about one to two seconds. If the first shock is unsuccessful, the electrode need not return completely to its rest position prior to delivering a second shock. The electrode may be returned to its completely deployed position from whatever state it is in when fibrillation is redetected.

Figure 3:
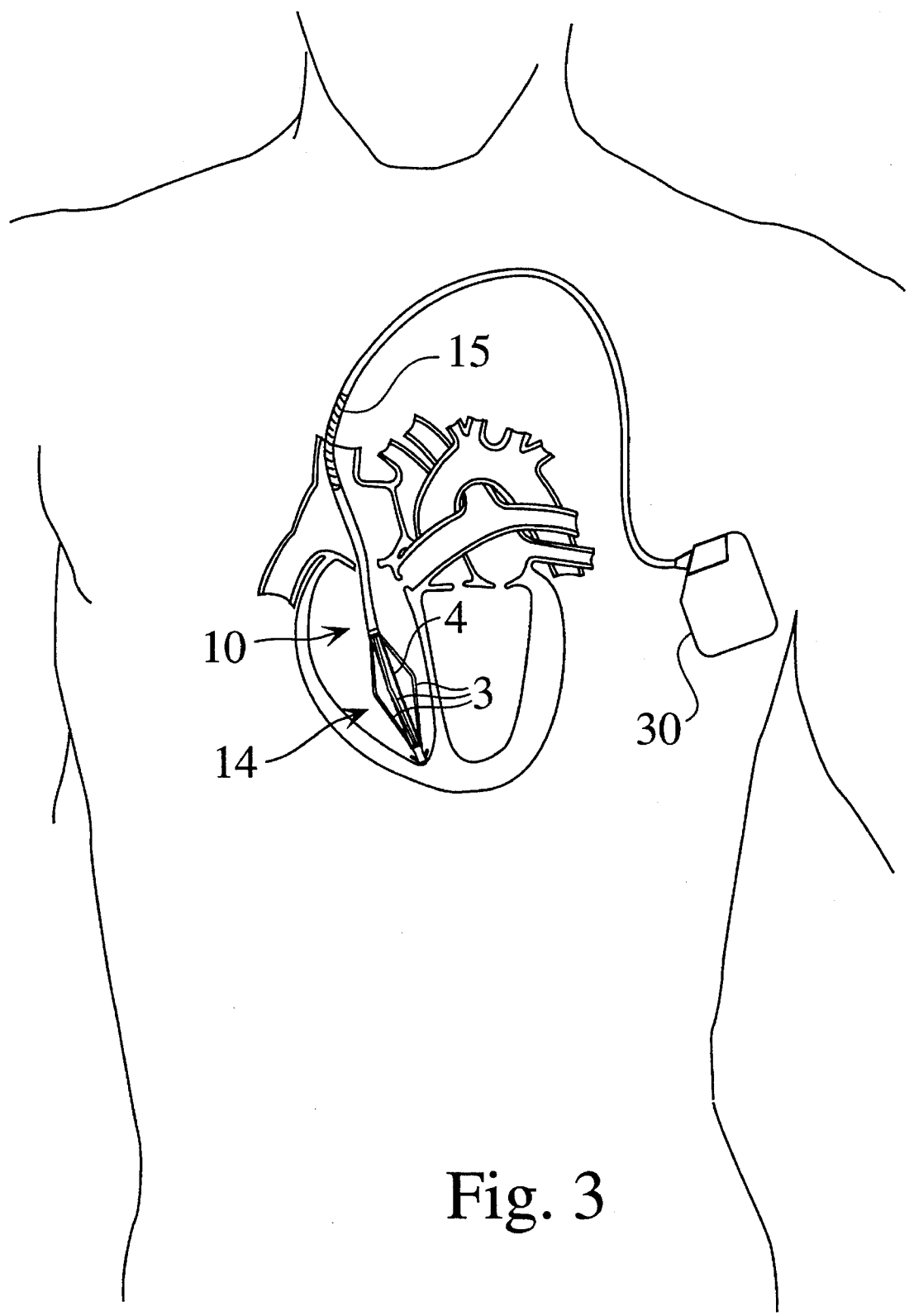
FIG. 3 is a perspective view of the lead of FIG. 1 having an electrode deployed by artificial muscle for defibrillation in position in the right ventricle of a patient's heart.

FIG. 3 shows lead 10 of FIG. 1 plugged into a pulse generator 30, and implanted within a patient. The right ventricle and right atrium of the heart are shown with the tricuspid valve between them. The inventive lead shown includes an RV defibrillation electrode 14 and an SVC defibrillation electrode 15, for positioning in or near the SVC. Only the RV electrode can be expanded and collapsed. One reason it is desirable that the electrode remain collapsible is that an uncollapsible structure could damage the tricuspid valve or other structures during explantation.

Several sizes may be offered to provide optimal fit to the patient's heart. Alternatively or additionally, the voltage applied to deploy the electrode may be selected to expand the electrode to the appropriate size for each patient. As yet another alternative, a mechanical stop may be provided on the lead body that can be adjusted by the physician to fit each patient.

Principal advantages of the deployable electrode are that it provides a variable electrode surface geometry that more effectively directs current through the heart muscle with less current being shunted through the blood pool, thus increasing the current density and energy throughout the heart muscle to depolarize the greatest amount of cardiac tissue at the lowest possible voltage.

It should be understood that various alternatives to the embodiments of the invention described herein may be employed in practicing the invention. For example, the artificial muscle deployment mechanism may be used for deploying a mapping electrode system during electrophysiology studies. It is thus intended that the following claims define the scope of the invention and that structures and methods within the scope of these claims and their equivalents be covered thereby.

What is claimed is:

1. A deployment mechanism for an implantable deployable electrode, comprising:
   at least one artificial muscle element mechanically coupled to the deployable electrode; and
   means for applying a voltage across said artificial muscle element causing said artificial muscle element to contract such that the deployable electrode is deployed.

2. The deployment mechanism of claim 1, further comprising an insulation means for electrically insulating said artificial muscle element from the deployable electrode.

3. The deployment mechanism of claim 1, and further including means for enhancing the return of the deployable electrode to its initial condition.

4. The deployment mechanism of claim 3, wherein said means for enhancing the return of the deployable electrode includes a spring.

5. The deployment mechanism of claim 3, wherein said means for enhancing the return of the deployable electrode includes means for reversing the polarity of the voltage across said artificial muscle element.

6. The deployment mechanism of claim 1, wherein said artificial muscle element comprises a polyelectrolyte gel.

7. The deployment mechanism of claim 1, wherein said artificial muscle element comprises a material selected from the group consisting of:
   poly(2-acrylamido-2-methylpropanesulfonic acid) (PAMPS) gel and polyacrylic acid plus sodium acrylate cross-linked with bisacrylamide (PAAM).

8. A lead for implantation in a patient comprising:
   a connector at a proximal end of said lead for connection to a pulse generator;
   a lead body having an insulated conductor electrically coupled to said connector;
   a deployable electrode electrically coupled to said conductor;
   an artificial muscle element mechanically coupled to said deployable electrode; and
   means for applying a voltage across said artificial muscle element causing said artificial muscle element to contract such that said deployable electrode is deployed.

9. The lead of claim 8, wherein said means for applying a voltage comprises a first artificial muscle element conductor electrically coupled to a first end of said artificial muscle element and a second artificial muscle element conductor electrically coupled to a second end of said artificial muscle element.

10. The lead of claim 8, further comprising an insulation means for electrically insulating said artificial muscle element from said deployable electrode.

11. The lead of claim 8, and further including means for returning the deployable electrode to its initial condition.

12. The lead of claim 11, wherein said means for returning the deployable electrode includes a spring.

13. The lead of claim 11, wherein said means for returning the deployable electrode includes means for reversing the polarity of the voltage across said artificial muscle element.

14. The lead of claim 8, wherein said artificial muscle element comprises a polyelectrolyte gel.

15. The lead of claim 8, wherein said artificial muscle element comprises a material selected from the group consisting of:
   poly(2-acrylamido-2-methylpropanesulfonic acid) (PAMPS) gel and polyacrylic acid plus sodium acrylate cross-linked with bisacrylamide (PAAM).

16. A stimulation system, comprising:
   a pulse generator for generating electrical energy;
   a lead having a deployable electrode electrically connected to said pulse generator and at least one artificial muscle element for expanding said deployable electrode from a nondeployed state to a deployed state; and
   control means for sensing an episode requiring therapeutic electrical pulses and for supplying a voltage across said artificial muscle element to deploy said deployable electrode during said episode and for causing said pulse generator to generate said therapeutic electrical pulses through said deployable electrode.

17. The cardiac stimulation system of claim 16, wherein said deployable electrode comprises an endocardial right ventricular defibrillation electrode.

18. The cardiac stimulation system of claim 16, wherein said lead further includes a nondeployable defibrillation electrode.

19. The cardiac stimulation system of claim 16, wherein said artificial muscle element comprises a polyelectrolyte gel.

20. The cardiac stimulation system of claim 16, wherein said artificial muscle element comprises a material selected from the group consisting of:
   poly(2-acrylamido-2-methylpropanesulfonic acid) (PAMPS) gel and polyacrylic acid plus sodium acrylate cross-linked with bisacrylamide (PAAM).

21. The cardiac stimulation system of claim 16, wherein said control means further includes means for adjusting the amount of voltage supplied across said artificial muscle element to control the degree to which said deployable electrode is deployed.

22. A method for deploying an electrode in a patient comprising the steps of:
   (a) providing at least one artificial muscle element mechanically attached to the electrode; and
   (b) applying a voltage across said artificial muscle element to cause said artificial muscle element to contract and deploy the electrode.

23. The method of claim 22, wherein the voltage applied in step (b) is 10 volts or less.

24. A method for defibrillating a patient's heart comprising the steps of:
   (a) applying a voltage across at least one artificial muscle element to deploy a defibrillation electrode; and
   (b) delivering a defibrillation pulse through the defibrillation electrode.

25. The method of claim 24 and further including the step of:
   (c) returning the defibrillation electrode to its initial position.

26. The method of claim 24 wherein the voltage applied in step (a) is 10 volts or less.

* * * * *